(12) United States Patent
Bachmaan et al.

(10) Patent No.: US 10,094,425 B2
(45) Date of Patent: Oct. 9, 2018

(54) HYDRODYNAMIC BEARING, AND X-RAY TUBE, AND X-RAY SYSTEM, AND A METHOD FOR MANUFACTURING A HYDRODYNAMIC BEARING,

(71) Applicant: KONINKLIJKE PHILIPS N.V., Eindhoven (NL)

(72) Inventors: Peter Klaus Bachmaan, Aachen (DE); Anand Kumar Dokania, Utrecht (DE); Wilhelmus Cornelis Keur, Weert (NL); Gereon Vogtmeier, Aachen (DE); Willem Potze, Geldrop (NL); Christian Herbert Blome, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 133 days.

(21) Appl. No.: 15/312,340

(22) PCT Filed: Apr. 1, 2015

(86) PCT No.: PCT/EP2015/057201
§ 371 (c)(1),
(2) Date: Nov. 18, 2016

(87) PCT Pub. No.: WO2015/176861
PCT Pub. Date: Nov. 26, 2015

(65) Prior Publication Data
US 2017/0097049 A1    Apr. 6, 2017

(30) Foreign Application Priority Data

May 21, 2014    (EP) .................................. 14169283

(51) Int. Cl.
*A61B 6/00*    (2006.01)
*F16C 39/02*    (2006.01)
(Continued)

(52) U.S. Cl.
CPC ............ *F16C 39/02* (2013.01); *F16C 17/026* (2013.01); *F16C 17/045* (2013.01);
(Continued)

(58) Field of Classification Search
CPC ............ H01J 35/101; H01J 2235/1086; H01J 2235/1066
See application file for complete search history.

(56) References Cited

U.S. PATENT DOCUMENTS

| 3,684,678 A | 8/1972 | Beardmore |
| 5,181,235 A | 1/1993 | Ono |

(Continued)

FOREIGN PATENT DOCUMENTS

| EP | 0600468 A1 | 6/1994 |
| GB | 794902 A | 5/1958 |

(Continued)

OTHER PUBLICATIONS

Miyoshi, Kazushisa et al NASA Technical Memorandum 104478, Jan. 1992.
(Continued)

*Primary Examiner* — Dani Fox
(74) *Attorney, Agent, or Firm* — Larry Liberchuk (57) ABSTRACT

The present invention relates to hydrodynamic bearings, X-ray tubes, X-ray systems, and a method of manufacturing a hydrodynamic bearing for an X-ray tube. The rotor of a hydrodynamic bearing is supported, in steady-state operation, by the pressure of lubricant which is pumped through grooves in the rotor. When the rotor is speeding up or slowing down, the pumping force will not be sufficient to lift the rotor clear of a stationary bushing, and damage, caused by direct contact of the metal surfaces of the bearing, can occur. Providing special coatings on the bearing surfaces can ameliorate this effect.

13 Claims, 9 Drawing Sheets

(51) Int. Cl.
*F16C 17/02* (2006.01)
*F16C 17/10* (2006.01)
*F16C 17/04* (2006.01)
*F16C 33/12* (2006.01)
*F16C 43/02* (2006.01)
*G01N 23/04* (2018.01)
*H01J 35/06* (2006.01)
*H01J 35/10* (2006.01)

(52) U.S. Cl.
CPC .......... *F16C 17/107* (2013.01); *F16C 33/124* (2013.01); *F16C 33/125* (2013.01); *F16C 43/02* (2013.01); *G01N 23/04* (2013.01); *H01J 35/06* (2013.01); *H01J 35/101* (2013.01); *F16C 2202/54* (2013.01); *F16C 2206/04* (2013.01); *F16C 2223/30* (2013.01)

(56) References Cited

U.S. PATENT DOCUMENTS 5,366,298 A 11/1994 Toshimitsu
5,384,819 A * 1/1995 Ono ................. F16C 17/026
                                                        378/125
5,624,191 A 4/1997 Fuchs
2010/0246773 A1 9/2010 Hunt

FOREIGN PATENT DOCUMENTS

| JP | 11213927 A | 8/1999 |
| JP | 2002025483 A | 1/2002 |
| JP | 2002075259 A | 3/2002 |
| WO | 2013046083 A1 | 4/2013 |

OTHER PUBLICATIONS

Gao, F. et al "The Tribological Properties of Low-Friction Hydrogenated Diamond-like Carbon Measured in Ultrahigh Vacuum", Tribology Letters, vol. 20, Nos. 3-4, Dec. 2005.

Konicek et al "Table 1, Origin of Ultralow Friction and Wear in Ultrananocrystalline Diamond", 2008.

* cited by examiner

HYDRODYNAMIC BEARING, AND X-RAY TUBE, AND X-RAY SYSTEM, AND A METHOD FOR MANUFACTURING A HYDRODYNAMIC BEARING,

CROSS-REFERENCE TO PRIOR APPLICATIONS

This application is the U.S. National Phase application under 35 U.S.C. § 371 of International Application No. PCT/EP2015/057201, filed on Apr. 1, 2015, which claims the benefit of European Patent Application No. 14169283.0, filed on May 21, 2014. These applications are hereby incorporated by reference herein.

FIELD OF THE INVENTION

The invention relates to a hydrodynamic bearing for an X-ray tube, an X-ray tube with a hydrodynamic bearing, an X-ray imaging system, and a method for manufacturing a hydrodynamic bearing.

BACKGROUND OF THE INVENTION

Hydrodynamic bearings are often used when a bearing is subject to demanding performance conditions. In a hydrodynamic bearing, a gap between a rotor and a stator is formed. The gap contains a lubricant. The rotor is provided with a network of grooves. Therefore, as the rotor rotates, a fluid dynamic pressure is generated within the gap. The pressure acts to raise the rotor in the bearing, thereby preventing contact between the rotor and the stator.

WO 2013/046083 A1 discloses a hydrodynamic bearing for an X-ray tube, comprising a bearing shaft and a bearing bushing. The bearing bushing encloses the bearing shaft concentrically, and is rigidly connected to an anode disc and to a rotor. In addition, the bearing bushing is rotatably arranged on the bearing shaft. The bearing shaft and the bearing bushing are rotatable with respect to one another.

The properties of such hydrodynamic bearings can still be further optimized.

SUMMARY OF THE INVENTION

Thus, there may be a need to provide a hydrodynamic bearing which is capable of withstanding faster rotation speeds whilst increasing the lifetime of the bearing.

The object of the present invention is solved by the subject-matter of the independent claims, wherein further embodiments are incorporated into the dependent claims.

It should be noted that the following described aspects of the invention apply also to an X-ray tube containing a hydrodynamic bearing, an X-ray imaging system containing such an X-ray tube, and to a method for manufacturing a hydrodynamic bearing.

According to the present invention, a hydrodynamic bearing for an X-ray tube with a rotatable anode is provided. The hydrodynamic bearing comprises a rotatable shaft for supporting the rotatable anode, a supporting bushing arranged to seal a length of the shaft, and a bearing arrangement provided between the shaft and the bushing. The bearing arrangement comprises a primary bearing mechanism and a secondary bearing mechanism.

The shaft is rotatably supported by the bearing arrangement in relation to the bushing. The primary bearing mechanism comprises a plurality of grooves in a surface of the supporting bushing, and/or the shaft. A lubrication material is contained within a sealed space between the rotatable shaft and the supporting bushing. The grooves are operable to interact with the lubrication material, and the primary bearing mechanism supports the rotatable shaft during a steady operating phase of the rotatable anode.

The secondary bearing mechanism comprises first bearing surface portions on the surface of the supporting bushing, and second bearing surface portions on the rotatable shaft. The first and second bearing surface portions are arranged opposite to each other, and the first and second bearing surface portions are provided as mutual contact surface portions. The secondary bearing mechanism supports the rotatable shaft during a starting and a landing phase of the rotatable anode. The first and second surface portions of the secondary bearing mechanism do not contact each other during the steady operating phase. At least a part of the first and/or second bearing surface portions comprises a first bearing coating, having a lower coefficient of sliding friction and a higher wear resistance, compared to a basis material of the shaft and/or a basis material of the bushing.

Hydrodynamic bearings for use in X-ray tubes, also known as spiral groove bearings or self-lubricating bearings, are constructed from parts made of metal. The lubrication between moving parts is facilitated by liquid metals or liquid eutectic alloy, which are able to withstand high temperatures. liquid eutectic alloy lubrication effectively reduces friction between the moving parts of the bearing during operation.

A problem that occurs, though, is that damage to the bearing surfaces occurs when the bearing begins rotational movement, and when the bearing finishes its rotational movement. In a steady state of operation, a hydrodynamic force is generated by the pumping action of the grooves on the lubrication material. The pumping action generates a force in opposition to the weight of the rotatable anode, thus lifting the rotatable anode clear of the bearing surfaces.

During startup and stopping of the hydrodynamic bearing, the lift force provided by the pumping action does not overcome the weight of the rotatable anode.

Therefore, the rotatable shaft comes into contact with the supporting bushing. This inevitably leads to damage of the bearing surfaces, due to material being abraded, and dislodged from the bushing or the rotatable shaft. Such mechanical contact may be worsened if the rotatable shaft lands at a tilt with respect to the supporting bushing.

The wear limits the lifetime of the hydrodynamic bearing. Faster rotation speeds of such rotatable anode X-ray tubes are continually required, owing to the demand for more powerful X-ray beams in various application areas. Therefore, the damage-free landing speed must be as high as possible.

The hydrodynamic bearing according to the invention provides the possibility of reducing the friction experienced by the rotatable shaft and the supporting bushing of the hydrodynamic bearing. This is achieved by coating at least a part of the first and/or second bearing surface portions with a first bearing coating which has a lower coefficient of sliding friction, and a higher resistance, compared to the basis material of the shaft or the bushing, respectively.

According to another embodiment of the invention, an X-ray tube is provided comprising a hydrodynamic bearing, as previously described, and a cathode. The cathode is connected to an anode disc. The cathode is configured to emit electrons towards the anode disc. The anode disc provides a rotatable surface which is configured to generate X-rays as a result of electrons emitted by the cathode impinging on the rotatable disc.

Therefore, an X-ray tube according to the invention will benefit from a longer operating life, because it uses a hydrodynamic bearing with the advantageous properties described above.

According to the invention, an X-ray imaging system is provided. The X-ray imaging system comprises an X-ray tube, an X-ray detector, a support for receiving an object, and a processing device. The X-ray tube is adapted for generating X-ray radiation. The X-ray detector is also adapted to receive the X-radiation after the radiation passes the object on the support.

According the invention, a method is provided for manufacturing a hydrodynamic bearing for an X-ray tube. The method comprises the steps of:
(a) providing untreated bearing shaft and bearing bushing parts,
(b) depositing a first bearing coating on at least a part of either the untreated bearing shaft, the untreated bearing bushing, or both, wherein the first coating has a lower coefficient of sliding friction, and a higher wear resistance, compared to a basis material of the shaft and/or a basis material of the bushing,
(c) assembling the bearing shaft and bearing bushing parts into a hydrodynamic bearing,
(d) adding a lubrication material,
(e) vacuum sealing the bearing.

According to the invention, a method is provided for manufacturing a hydrodynamic bearing for an X-ray tube, which has a longer life.

The term "primary bearing mechanism" refers to the pumping action of the lubrication material in the grooves. It should be noted that the grooves can be provided either in the rotatable shaft or the supporting bushing, or both. As the rotatable shaft increases in speed, the lift provided by the primary bearing mechanism increases, and so it overcomes the weight of the rotatable anode supported by the rotatable shaft. At this point, the primary bearing mechanism lifts the rotatable shaft, and thereby the rotatable anode, in the supporting bushing, such that substantially no part of the rotatable shaft is in contact with the supporting bushing.

The term "secondary bearing mechanism" refers to the situation where the lift force caused by the pumping action on the rotatable shaft is overcome by the weight of the rotatable shaft and the supporting bushing, and therefore the rotatable shaft begins to contact the supporting bushing. In this case, a friction force will be produced as the rotatable shaft rotates in contact with the supporting bushing. The friction force is present when the bearing is starting from a stopped state and when the bearing is stopping from a started state.

In other words, the primary bearing mechanism is caused by the pumping action of the lubricant in the grooves of the bearing.

In other words, the secondary bearing mechanism results from the physical contact of bearing components.

The term "steady operating phase" refers to a state of the hydrodynamic bearing where the rotation speed of the rotatable shaft is substantially constant, and the lift force generated by the pumping action on the rotatable shaft is balanced by the mass of the rotatable shaft holding the rotatable anode off the X-ray tube. Thus, in the steady operating phase, there is no contact between the rotatable shaft and the supporting bushing. The term "first bearing surface portions" refers to any area of the supporting bushing, or to a smaller portion of the surface of the supporting bushing. Likewise, the term "second bearing surface portions" refers to any part of the rotatable shaft, or to a selected area of the rotatable shaft.

In other words, an aspect of this invention is the use of a low wear and low friction coating in a hydrodynamic bearing suitable for use in medical X-ray tubes, to protect the surface of the hydrodynamic bearing and thus to reduce damage to the tube.

It shall be understood that the hydrodynamic bearing for an X-ray tube, the X-ray tube with a hydrodynamic bearing, the X-ray imaging system and the method for manufacturing a hydrodynamic bearing according the independent claims have similar and/or identical preferred embodiments, in particular, as defined in the dependent claims. It shall be understood further, that the preferred embodiment of the invention can also be in any combination of the dependent claims with its respective independent claim.

These and other aspects of the present invention will become apparent from, and be elucidated with reference to, the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
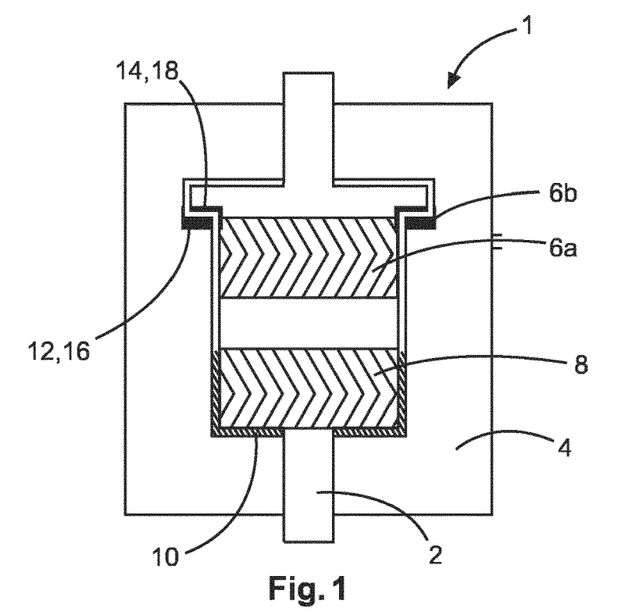
FIG. 1 schematically shows a cross-sectional view of a self-lubricating sliding bearing according to an embodiment of the invention.

FIG. 1 schematically shows a hydrodynamic bearing 1 for an X-ray tube with a rotatable anode. The hydrodynamic bearing comprises a rotatable shaft 2 for supporting the rotatable anode, a supporting bushing 4 arranged to seal a length of the shaft, and a bearing arrangement 6 provided between the shaft and the supporting bushing, comprising a primary bearing mechanism 6a and a secondary bearing mechanism 6b, wherein the shaft is rotatably supported by the bearing arrangement in relation to the bushing.

In addition, the primary bearing mechanism comprises a plurality of grooves 8 in a surface of the supporting bushing and/or the shaft, and a lubrication material 10, contained within a sealed space between the shaft and the supporting bushing. The grooves 8 are operable to interact with the lubrication material 10, and the primary bearing mechanism 6a supports the rotatable shaft 2 during a steady operating phase of the rotatable anode.

In addition, the secondary bearing mechanism 6b comprises first bearing surface portions 12 on the surface of the supporting bushing, and second bearing surface portions 14 on the rotatable shaft 2. The first and second bearing surface portions are arranged opposite to each other.

The first bearing surface portions 12 may alternatively be designated a thrust disc, or a spacer ring. The second bearing surface portions 14 may alternatively be designated a collar, or a bushing.

As will become apparent, the secondary bearing mechanism has a dual purpose. Firstly, the first and second bearing surface portions are provided as mutual contact surface portions, wherein the secondary bearing mechanism supports the rotatable shaft physically during a starting and a landing phase of the rotatable anode.

The first and second surface portions of the secondary bearing mechanism 6b do not contact each other during a steady operating phase.

The secondary bearing mechanism is also provided with means for pumping the lubrication material 10 in the steady operating phase. The means may be provided on the first bearing surface portion 12, the second bearing surface portion 14, or on both. At least a part 16 of the first and/or second bearing surface portions comprise a first bearing coating 18 having a lower coefficient of sliding friction and a higher wear resistance, compared to a basis material of the shaft and/or a basis material of the supporting bushing 4. The bearing supporting bushing 4 may also be denoted as a sleeve, and concentrically encloses the bearing's rotatable shaft 2. An anode disc may be connected to the bushing 4 in such way that it rotates at the same velocity as the bearing bushing.

According to an alternative embodiment, it will be appreciated that an outer member (in the place of the supporting bushing) of the bearing may rotate, and an inner member of the bearing (in the place of the rotatable shaft) may remain stationary. In this case, the rotatable anode's disc may be connected to the rotatable outer member of the alternative bearing. Apart from this difference, the bearing is provided with grooves and a lubrication material, and encloses a vacuum, such that the primary and secondary bearing mechanisms operate in the same way. A bearing manufactured according to this alternative embodiment will function according to the same first and second bearing mechanisms described herein, and the benefits accruing from the use of at least a first bearing coating on at least a first bearing portion of such an alternative embodiment will still be attained.

The end of the rotatable shaft not connected to an anode is connected to a motor operable to rotate the rotatable shaft of the hydrodynamic bearing and thereby to rotate the rotatable anode in the X-ray tube, when the hydrodynamic bearing is incorporated in an X-ray tube.

The supporting bushing comprises first bearing surface portions 12 on the surface of the supporting bushing. In FIG. 1, the first bearing surface portions are shown in a recess in the supporting bushing 4. It will, however, be appreciated that the first bearing surface portions may be distributed anywhere on the inside of the supporting bushing, for example the entire internal surface of the bushing may be regarded as the first bearing surface portion, only the sides of the supporting bushing or only the top surface of the supporting bushing.

Likewise, the rotatable shaft 2 comprises second bearing surface portions 14. In FIG. 1, these are shown on the extending portion of the rotatable shaft 2. It will, though, be appreciated that the second bearing surface portions may be designated on any part of the rotatable shaft 2. For example, the second bearing surface portions may cover substantially the entire rotatable shaft 2. Alternatively, the second bearing surface portions may only be designated on the lower surface of the rotatable shaft. Alternatively, the second bearing surface portions may be designated only in the middle area of the rotatable shaft.

The bearing is also provided with means for pumping the lubrication material 10 in such a way as to cause the rotating shaft to float on the lubrication material. This means is not visible in FIG. 1 or 2.

Figure 3:
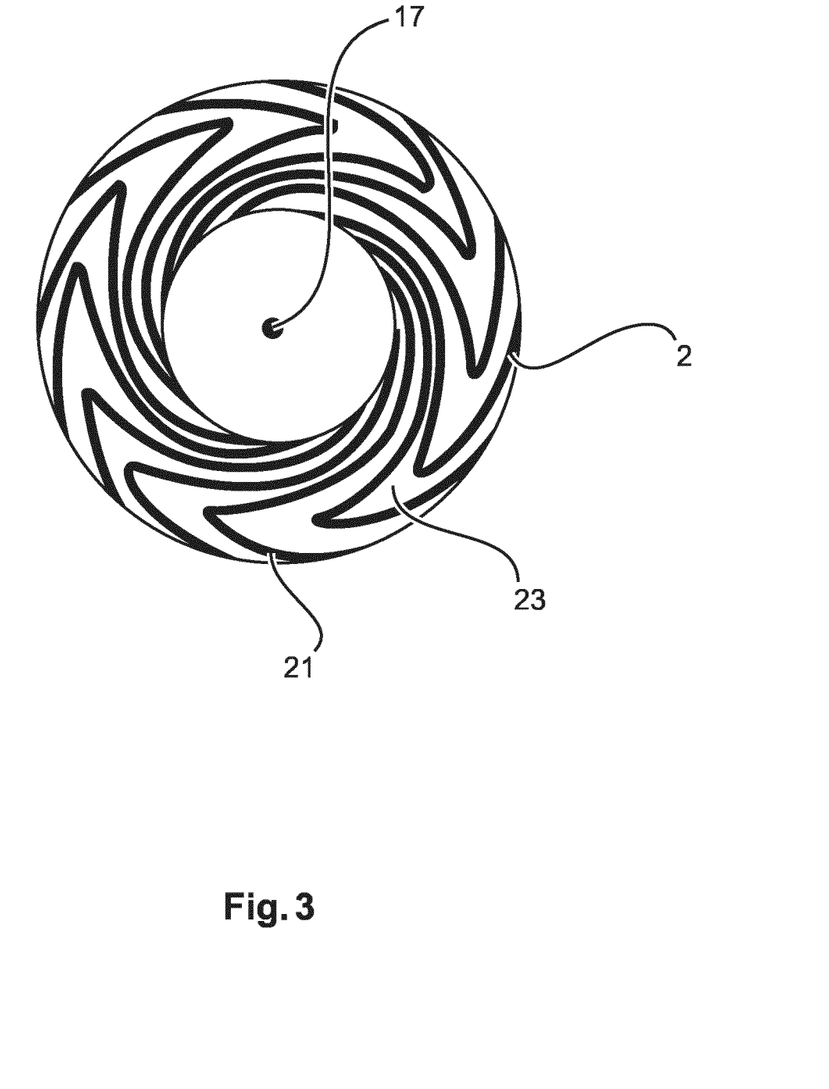
FIG. 3 shows an end-view of an example of a spiral groove thrust bearing.

FIG. 3 provides an "end-on" view of an example of the rotating shaft 2, primarily to illustrate the means for pumping the lubrication material 10 to lift the bearing. Feature 17 is the axis of rotation of the rotating shaft 2. The portion of the rotating shaft 2 forming the axial bearing of the primary bearing mechanism is provided with the ridges 21 and grooves 23, which together form a spiral groove bearing (thrust bearing). The ridges and grooves may, alternatively, or in addition, be arranged on the relevant portion of the bushing. The first bearing surface portions 12 and the second bearing surface portions 14 are arranged opposite to each other, wherein the first and second bearing surface portions are arranged as mutual contact surface portions. As shown in FIG. 1, the second bearing surface portion 14 is directly above the first bearing surface portions 12. Alternatively, the first bearing surface portions 12 and the second bearing surface portions 14 could be arranged opposite each other on the sidewall of the supporting bushing and the rotatable shaft or on the bottom surface of the rotatable shaft and the supporting bushing. It is to be noted that many other variations meeting this condition will be envisaged by the skilled reader, and the examples discussed in this paragraph serve merely as non-limiting examples.

At least one of the bearing faces comprises a plurality of grooves 8. The cross-section of the grooves may be constant, or the cross-section of the grooves may vary along the longitudinal direction of the groove.

In FIG. 1, grooves 8 are arranged on the rotatable shaft 2 of the bearing, and on both surfaces (or in variations, the bottom surface, or the top surface only) of the collar of the rotatable shaft 2. The spiral grooves forming the thrust bearing (axial bearing) on the bottom surface of the collar of the rotatable shaft 2 are not visible in the side-view of FIG. 1. The plurality of grooves 8 may comprise at least two separate regions of grooves, as displayed in FIG. 1. A first, upper, band of grooves and a second, lower, band of grooves may be provided on the rotatable shaft 2. Furthermore, the plurality of grooves 8 may be arranged at a predefined distance to each other, also denoted as groove/ridge ratio. The number of grooves 8 on the bushing surfaces may be chosen such that at a certain groove/ridge ratio, the supporting bushing's surfaces are completely covered by the curved grooves.

Thus, a cylindrical (concentric) gap is provided between the rotatable shaft 2 and the supporting bushing 4. The width of the gap may be in the range of 1 to 100 µm and is, in the following, denoted as the bearing gap.

A lubricant such as a metal eutectic is contained in the grooves, and in the bearing gap. The metal eutectic is a eutectic alloy, which is liquid at room temperature and at a temperature of up to 1300° C. The metal eutectic may comprise at least one of gallium, indium and tin. For example, the metal eutectic may be "galinstan", which comprises gallium, indium and tin. The metal eutectic may, when melted, act as a lubricant, and at the same time as a thermal contact to provide, for example, cooling of the bushing or the rotatable shaft. The metal eutectic also conducts electricity, and provides an electrical return-path for the current applied to the rotating anode. Of course, other lubricants with suitable fluid performance for use in a hydrodynamic bearing could be used, without adverse effect.

During steady-state operation at a nominal operation velocity or speed of the hydrodynamic bearing 1, such as 200 Hz, (in a mode in which the primary bearing mechanism supports the rotatable shaft 2), the lubrication material 10 is exposed to the pumping action of the grooves, and this causes pressure conditions that cause a hydrodynamic lubricant film to be formed.

Therefore, the bearing surfaces of the rotatable shaft 2 and the supporting bushing 4 are not in contact with each other. The pumping action relies on the relative movement of the bearing part surfaces with respect to each other, and at least the partial wetting of such surfaces by the liquid eutectic alloy.

The basis material from which the rotatable shaft 2 and the supporting bushing 4 are made is usually molybdenum, steel, or tungsten. Alloys could also be used.

The operation of the hydrodynamic bearing 1 in the context of an X-ray tube will now be described.

Initially, the hydrodynamic bearing 1 is inactive, and thus the rotatable shaft 2 does not move with respect to the supporting bushing 4. The grooves 21 of the rotatable shaft are in contact with the supporting bushing 2.

A motor connected to the rotatable shaft 2 is initiated and gradually increases in speed until the rotatable shaft 2 reaches its steady operating speed. During a first operation phase, otherwise denoted as a starting phase, a hydrodynamic bearing will operate according to a secondary bearing mechanism. At this point, insufficient pressure will be generated by the action of the lubrication material in the grooves of the rotatable shaft, or the supporting bushing. Therefore, there will not be enough lift force on the rotatable shaft 2 to lift it clear of the supporting bushing.

In this starting phase, a bottom surface of the rotatable shaft 2, and a lower surface of the supporting bushing 4, for example, are substantially in contact. Therefore, friction forces will be exerted. When the groove surfaces of the rotatable shaft 2 are at least partially wetted by the liquid eutectic alloy, the lubrication material will begin to be pumped through the spiral grooves 23, and the grooves 8.

A lift force on the rotatable shaft 2 is caused by the pressure exerted by the lubricant due to the pumping action of the grooves of the thrust bearing (axial bearing) on the collar of the rotatable shaft 2. As the rotating shaft 2 begins to turn, pressure is exerted on the rotating shaft 2 by the lubrication material (which is incompressible) as it is forced into the grooves. The grooves form a flow restriction, which may be amplified by using a spiral groove characteristic. Logarithmic spiral, and herringbone spiral characteristics are commonly used also, but the skilled person will be able to use others. The pressure in the fluid as it passes through the grooves causes it to exert an upward force on the rotating shaft 2. As the rotation speed increases, this force will be enough to lift the rotating shaft 2 into a position in the bearing where it is floating on a thin cushion of lubrication material. Thus, the bearing supports a load as it begins to turn. The rotation speed at which this occurs is influenced by the lift force generated by the spiral grooves, the bearing geometry, wetting interaction between the lubricating liquid eutectic alloy, bearing component surfaces, rotational speed, and surface velocity.

When the hydrodynamic bearing generates a load force sufficient to carry the rotatable parts (the rotatable shaft 2) of the hydrodynamic bearing, the rotatable shaft 2 will lift clear of the supporting bushing 4. This load carrying capacity is generated by the pressure differences in the lubricant generated by the interaction of the liquid eutectic alloy lubricant and the solid surfaces involved. Thus, the hydrodynamic bearing enters a second operating phase, referred to as a steady operating phase of the rotatable anode. In this phase, the rotatable shaft floats on the lubrication material 10. The first and second surface portions of the secondary bearing mechanism do not contact each other during the steady operating phase.

Fluid pumped by the grooves of the thrust bearing (axial bearing) flows into the space between the rotating shaft 2 and the supporting bushing 4. As stated, the surface either of the rotating shaft 2, or the supporting bushing 4, comprises further sets of grooves which, in operation, function to pump the lubrication material 10 back to the thrust (axial) bearing in a manner. In this way, a recirculation of the lubrication material 10 is established.

The pumping action in the axial bearing generates a pressure in the lubricant (fluid) such that the bearing surfaces are separated.

Finally, a stage of operation called the landing phase will be reached. In the landing phase, the rotation velocity of the rotatable shaft 2 is decreased. As the velocity is decreased, the lift force generated by the action of the lubrication material in the grooves of the thrust bearing (axial bearing) decreases commensurate with the decrease in velocity. Therefore, the mass of the rotatable shaft gradually acts to lower the rotatable shaft back into contact with the supporting bushing. Thus, in the landing phase the secondary bearing mechanism again becomes dominant. Thus, during starting and landing of the rotatable shaft, the pressure levels generated by the thrust bearing (axial bearing) is insufficient to avoid contact between the solid, moving metallic parts of the bearing.

As previously stated, particularly during the landing phase and, in particular, for advanced X-ray tubes which have high anode rotation speeds, significant impacts of the rotatable shaft 2 and the supporting bushing 4 cannot be completely avoided. Such impacts may lead to damage of the bearing. Friction welding might even occur, causing the destruction of the X-ray tube.

Thus, as previously stated, to overcome these problems, a hydrodynamic bearing 1 is provided wherein at least a part of the first and/or second bearing surface portions comprises a first bearing coating 18 having a lower coefficient of sliding friction and a higher wear resistance, compared to a basis material of the shaft and/or a basis material of the bushing.

Advantageously, the provision of a first bearing coating on the first, the second, or both bearing surface portions, which has a lower coefficient of sliding friction and a higher wear resistance, can reduce friction during the starting and landing phase of the rotatable anode, and resist wear when the rotatable shaft 2 comes into contact with the supporting bushing. Thus, the construction of a hydrodynamic bearing supported rotatable anode X-ray tube which is particularly useful in medical X-ray tubes is possible.

According to exemplary embodiments of the invention, the first and/or second bearing coatings may comprise, for example, at least one material selected from the list of molybdenum disulphide, amorphous carbon, tetrahedrally coordinated amorphous carbon, ultra nano crystalline diamond film, nano- and ultra-nano-crystalline vapour-deposited diamond, polycrystalline diamond, and tungsten disulphide.

Any combination of materials in the foregoing list may be used to provide the first and second bearing coatings.

Alternatively, the first and/or second bearing coatings may be formed from an arbitrary number of composite layers, formed from a plurality of materials from in the above list. For example, coatings with two, three, four, five, and six layers, with each layer selected from the above group, may be provided.

Any combination of materials in the foregoing list may be used to provide the composite layers.

Purely as an example, and with no limiting effect, the properties of these materials are discussed below.

A typical example of the coefficient of friction of a molybdenum disulphide coating film, measured in a vacuum, is 0.05, (before the stage where film failure is experienced), as stated in FIG. 5 of "A discussion of the use of molybdenum disulphide as a solid lubricant can be found in NASA Technical Memorandum 104478 of January 1992, authored by Kazushisa Miyoshi, Frank S. Honecy, Philip B. Abel, Steven V. Pepper, Talivaldis Spalvins, and Donald R. Wheeler".

A typical example of the coefficient of friction of a diamond-like carbon film, measured in a vacuum, is between 0.03 and 0.12, as stated in "The tribological properties of low-friction hydrogenated diamond-like carbon measured in ultrahigh vacuum" by F. Gao et. al, in "Tribology letters", Vol. 20, Nos 3-4, December 2005.

A typical example of the hardness of a ultra nano crystalline diamond film is more than 10 on the Mohs scale of mineral hardness.

A typical example of the coefficient of friction of an ultra-nano-crystalline diamond film, measured in a vacuum, is 0.015+/−0.002 ("Table 1, Origin of Ultralow Friction and Wear in Ultrananocrystalline Diamond", Konicek et. al, Departmental review paper of the University of Pennsylvania, Jul. 11, 2008).

A typical example of the hardness of a diamond-like carbon film is close to 10 on the Mohs scale of mineral hardness.

This can be compared to the hardness of the basis material of the bearing. Molybdenum has a hardness of about 5.5 Mohs, and tungsten, or hardened steel has a hardness of between 7.5 and 8 Mohs.

According embodiments of the invention, the friction coefficient of the first, and/or second bearing surfaces may lie in the range 0.1-0.5; 0.1-0.4; or 0.1-0.3 and may, more preferably, be below 0.3.

It will be appreciated that the first bearing coating may be applied in a continuous manner over the entirety of the rotatable shaft, or the supporting bushing.

Thus, the structure and operation of a simple hydrodynamic bearing according to the invention, and as schematically shown in FIG. 1, has been described. It will be appreciated by the skilled reader that many variations can be constructed which match the basic schematic concept shown in FIG. 1.

Figure 2:
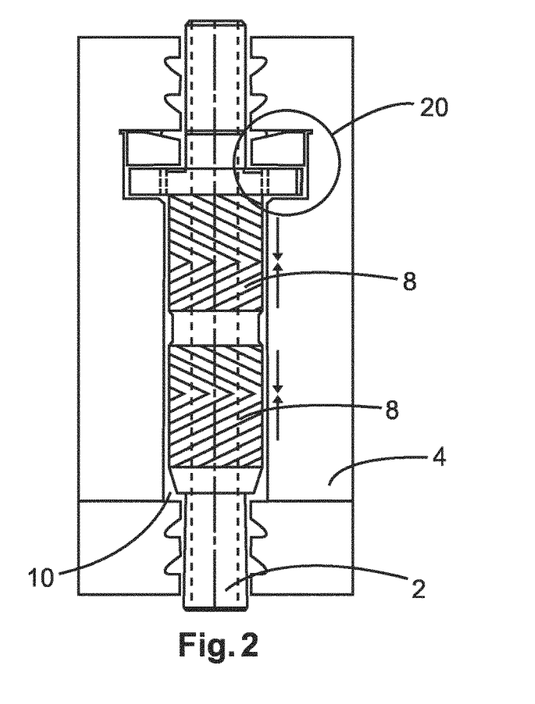
FIG. 2 shows a part of a conventional hydrodynamic bearing.

FIG. 2 shows a cross-section through a design of a conventional hydrodynamic bearing, used in practice. The rotatable shaft 2 of the illustrated bearing comprises two bands of grooves 8, separated by a central portion with no grooves. The inset 20 is illustrated further in FIG. 4A and FIG. 4B. In this case, the grooves 8 are in a herringbone pattern, but many other patterns could be used.

Figure 4A:
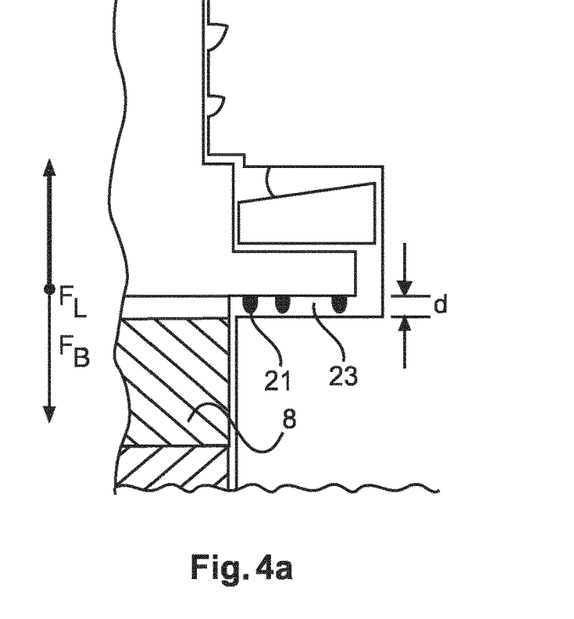
FIGS. 4A and 4B show a side view of an example of a hydrodynamic bearing before and after use.

FIG. 4A illustrates the conventional bearing of FIG. 2 in normal operation. It can be seen from this close-up view that the force caused by the mass of the bearing $F_b$ is overcome by force $F_l$, which originates in the pumping action of the lubrication material 10 in the grooves 23 of the thrust bearing (axial bearing). Therefore, there is a distance, d, (measured in the direction of the rotatable shaft's axis of rotation), between a first bearing surface portion 12 and a second bearing surface portion 14 on the surface portion of the supporting bushing. The forces of the pumping action from the thrust bearing (axial bearing) are illustrated by the vertical arrows in FIG. 4A.

Figure 4B:
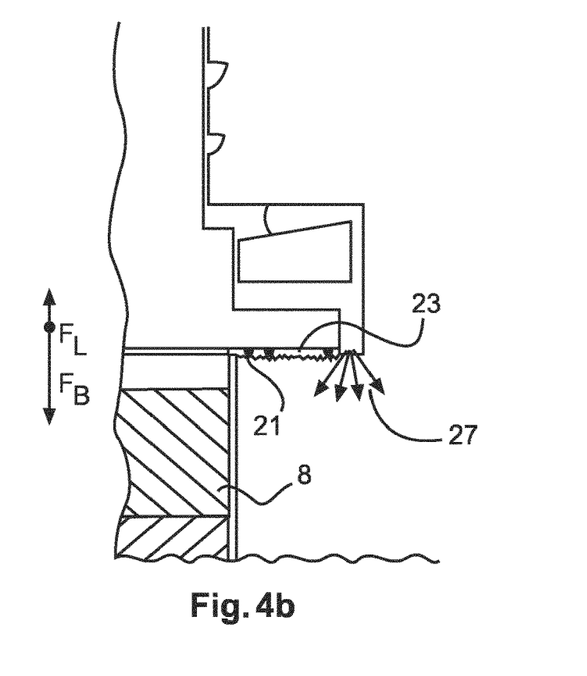

FIG. 4B shows a situation just after a landing phase of the rotatable anode. Because the rotatable shaft 2 has slowed down, the force caused by the mass of the rotatable shaft and anode has drawn the rotatable shaft downwards. Damaged areas 21 have been created on the supporting bushing 4, and on the ridges 23 of the thrust bearing (axial bearing).

This is a graphical illustration of a problem which the present invention overcomes. Such damage is undesirable because it could affect the fluid dynamic performance in the bearing. In extreme cases, there could be a catastrophic failure of the bearing, where the rotatable shaft 2 and the supporting bushing 4 are friction-welded together.

In addition, abraded fragments 27 may also become suspended in the metal lubricant. Such free-floating abraded parts could foul the motion or fluid flow in the hydrodynamic bearing at a later stage, or contribute to increased wear of the bearing. It is, therefore, important to reduce the risk of damage to the bearing's surfaces.

Of course, other parts of the rotating shaft 2 might also contact the supporting bushing 4, such as the ridges 8.

Figure 5A:
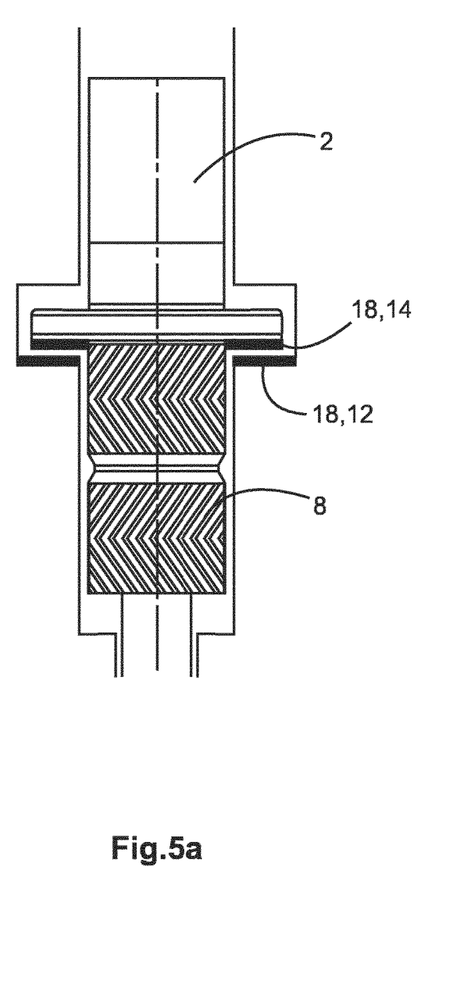
FIGS. 5A, 5B, and 5C show bearing coatings according embodiments of the invention.

FIG. 5A illustrates an embodiment of the invention, wherein the first bearing coating is applied to first and second surface portions of the secondary bearing mechanism and the rotatable shaft forming the thrust bearing (axial bearing). The coated areas are shown with a thick black line. As shown in FIG. 5A, the first bearing coating 18 may be located on a surface of the bushing 12 forming the thrust bearing (axial bearing).

Figure 5B:
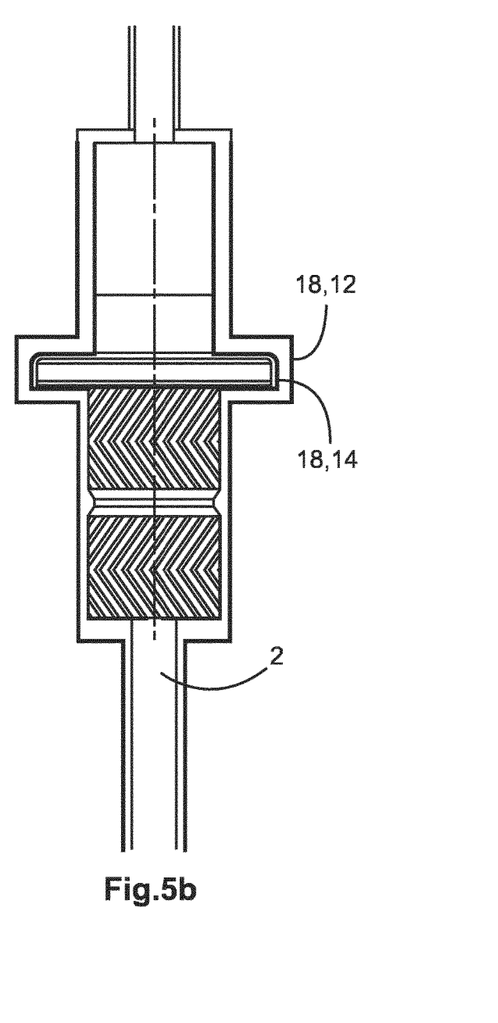

FIG. 5B shows an alternative embodiment of the invention. In FIG. 5B, substantially the entire surface of the supporting bushing 4 has been coated with the first bearing coating, and substantially the entire surface of the rotatable shaft 2 which does not comprise grooves has been coated with the first bearing coating. This is denoted by the thick black line.

Figure 5C:
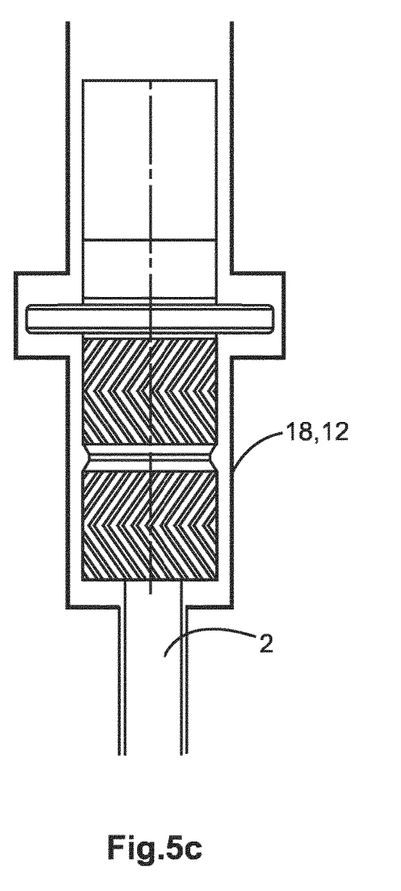

FIG. 5C shows yet another alternative embodiment of the invention using the first bearing coating 18. The first bearing surface portions 12 on the surface of the supporting bushing 4 are entirely coated with the first bearing coating, denoted by the thick black line. The rotatable shaft 2 does not have any coating.

In FIGS. 5A-5C, the grooves 21 of the thrust bearing (axial bearing) are not shown in profile, for the purposes of clarity. These diagrams are to provide a schematic indication of where the first bearing coating may be applied. The coating may be applied at other locations.

In another alternative embodiment, a portion of the rotatable shaft 2 may be provided with the first bearing coating, and the supporting bushing 4 may not be provided with the first bearing coating.

Advantageously, according to the foregoing embodiments, the first bearing coating reduces the friction between bearing parts when they are in contact during a start-up, or a landing phase. In addition, the parts are protected from wear. It will be appreciated that this advantage is amplified when two opposite bearing faces, both of which are coated with the first bearing coating, come into contact with each other.

According to an embodiment of the invention, a hydrodynamic bearing 1 is provided wherein the first bearing surface portions 12 and the second bearing surface portions 14 are coated with the first bearing coating 18, and the coated portions are arranged opposite to each other. According to this embodiment, the first bearing coatings on the rotatable shaft 2 and the supporting bushing 4 are arranged to come into contact during a starting and a landing phase of the rotatable anode.

Advantageously, this means that during the starting and landing phase, the surface of the hydrodynamic bearing 1 is protected from wear of the bearing parts, and the bearing parts experience a lower coefficient of sliding friction. Therefore, less damage occurs during the starting and landing phases. It will be appreciated, that the simultaneous provision of the first bearing coating on corresponding (opposite) surfaces further reduces the friction.

According to an embodiment of the invention, a hydrodynamic bearing 1 is provided wherein the second bearing surface portion 14 of the thrust bearing (axial bearing) comprises a second bearing coating 24 different in composition to the first bearing coating. Advantageously, in this embodiment bearing coatings of the rotatable shaft 2 and the supporting bushing 4 may be chosen to provide an optimal coating for both the shaft, and the supporting bearing.

Figure 6:
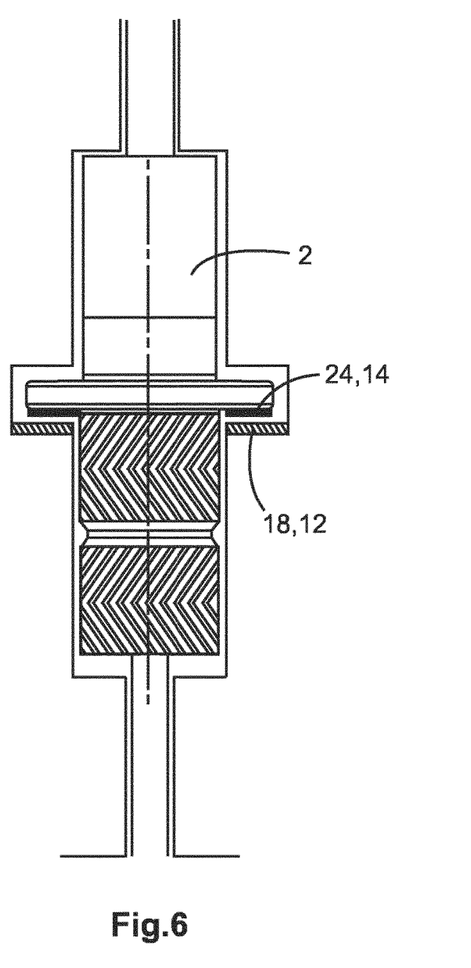
FIG. 6 shows bearing coatings according to an embodiment of the invention.

FIG. 6 illustrates a hydrodynamic bearing according to this embodiment. The second bearing surface portion of the thrust bearing (axial bearing) is coated with bearing coating 24 and the first bearing surface portion 12 of the thrust bearing (axial bearing) is coated with the first bearing coating 18. It will, also, be appreciated that a second bearing coating, different in composition to the first bearing coating, may be provided on any surface of the second bearing surface portion, either a portion of the surface, or indeed over the entire second bearing surface portion, in an analogous way to those illustrated in FIG. 5A. FIG. 6 illustrates an exemplary, non-limiting case where portions of the supporting bearing are coated in the second bearing coating 24, and portions of the rotatable shaft 2 are coated with the first bearing coating 18.

Advantageously, the use of different bearing coatings on the rotatable shaft 2 and the supporting bushing 4 may allow different coatings, customized to each component, to be applied. For example, the rotatable shaft 2 is likely to land at a tilt during the landing phase, and to "rattle" in the supporting bushing. Thus, a different type of wear may be imparted to the supporting bushing 4, compared to the rotatable shaft 2. According to this embodiment, coatings may be used which are tuned to the unique shocks that each part may experience in operation.

It is also to be noted that the basis materials of the rotatable shaft 2, and the supporting bushing 4, may be different. According to this embodiment, coatings may, advantageously, be provided which are compatible with different materials.

It will be appreciated that the operating requirements of the hydrodynamic bearing 1, such as high pressure and high temperature, lead to requirement for coatings which must fulfill complex and demanding tolerances. The coatings used in a hydrodynamic bearing according to the invention should be fully or partially wettable by the lubrication material to allow for pumping and pressure buildup in the bearing gap.

As stated previously, in an exemplary embodiment, the lubrication material is a gallium-indium-tin liquid eutectic alloy.

The coatings may exhibit a lower coefficient of friction than the metal surface of the uncoated bearing components when sliding on top of each other. The bearing coatings must be fairly resistant to corrosion by the liquid eutectic alloy lubricant. In addition, the coatings should exhibit a higher resistance to mechanical wear than the metal used for the bearing parts. The coatings must function and maintain their properties at temperatures of at least 200° C., preferably larger than 300° C., and in high vacuum conditions.

Finally, the bearing coatings must be applicable as a thin uniform coating on either the supporting bushing, the rotatable shaft, or both, in such a way as to avoid inhomogeneous pressure build-up in the bearing gap. Such inhomogeneous pressure build-up is induced by thickness and dimension variations when the coating is applied.

According to an embodiment of the invention, a hydrodynamic bearing 1 is provided as previously described, wherein at least one bearing coating is treated for compatibility with the lubrication material 10.

Thus, in the bearing with a first bearing coating, the first bearing coating is treated for compatibility with the lubrication material. In a bearing with a first bearing coating and a second bearing coating, both bearing coatings are treated for compatibility with the lubrication material.

According to an embodiment of the invention, a hydrodynamic bearing is provided wherein the grooves 8 comprise upper ridges 26, and the upper ridges 26 are treated with the first bearing coating.

Figure 7A:
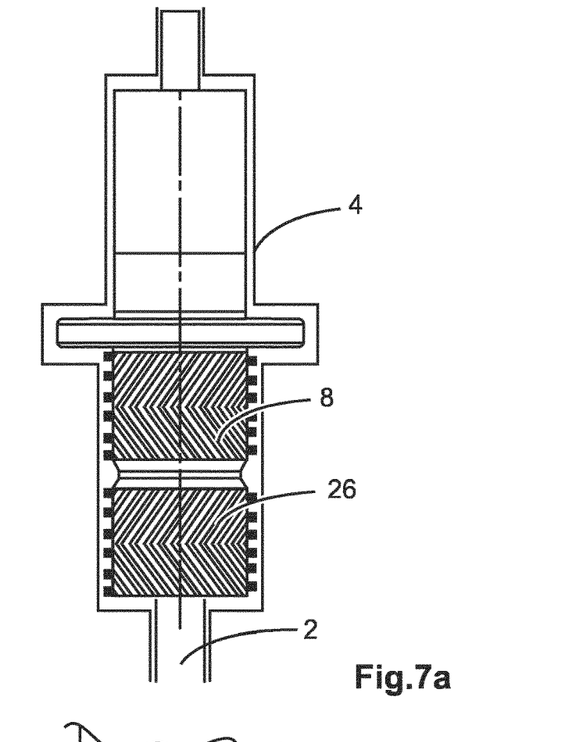
FIGS. 7A and 7B show side views of an exemplary hydrodynamic bearing.

FIG. 7A illustrates a hydrodynamic bearing according to this embodiment. In FIG. 7A, the rotatable shaft 2 and the surface bushing 4 are provided as previously described.

The radial surface of the rotatable shaft 2 comprises a plurality of grooves 8, distinct from the grooves 23 of the axial bearing on the "collar" of the rotatable shaft. As stated previously, the pumping action generated by the grooves 8 causes the recirculation of lubrication material 10 back to the thrust bearings (axial bearings). The grooves in the radial and axial bearing take care that the bearing delivers the required load capacity and that the lubricant remains inside the bearing gap. Also illustrated are the upper ridges 26 of the rotatable shaft groove arrangement.

When the hydrodynamic bearing transitions from a stationary to a steady-state mode, or vice versa, instabilities may cause the rotatable shaft 2 to rotate eccentrically around the central axis of the hydrodynamic bearing 1. The ridges 26 stand proud of the rotating shaft 2, and are, thus, likely to collide with the supporting bushing 4. Such a collision will cause detrimental erosion to the bearing parts, or even catastrophic failure.

Therefore, treatment of the ridges 26 and/or grooves 8 in an analogous manner to the treatment of the thrust bearings (axial bearings) discussed previously can reduce such detrimental effects.

Figure 7B:
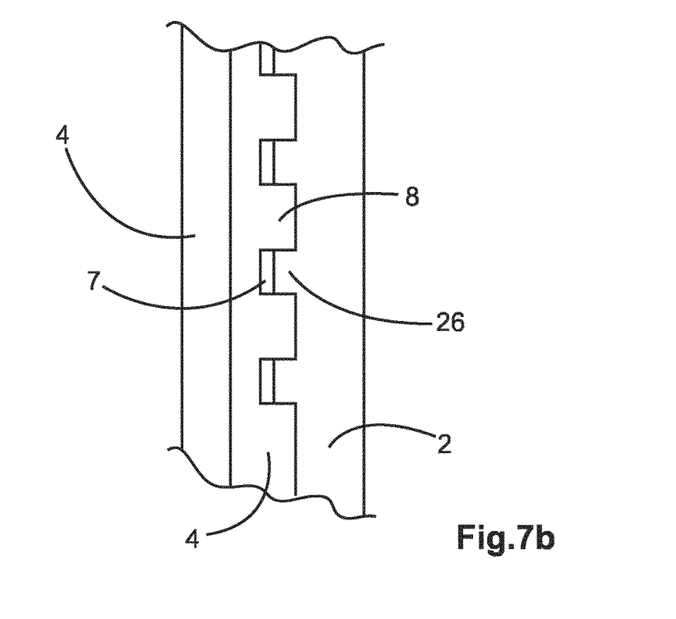

FIG. 7B illustrates more closely the surface a section of ridges 8 of the radial section of the hydrodynamic bearing according to an embodiment. The supporting bushing 4 and the rotatable shaft 2 enclose a space 9 which contains a lubrication material 10. This section of the rotatable shaft 2 comprises upper ridges 26 standing proud of grooves 8. The upper ridges 26 are coated with the first bearing coating 7. This coating may be any suitable friction-reducing and wear-resistant coating, as discussed in this application, although the use of others will occur to the skilled person.

In this case, the surface of the molybdenum base material of the bearing is coated as described earlier, with a uniform low wear and low friction coating. As an example, a layer of amorphous carbon about 5 um thick may be deposited on a cylindrical molybdenum blank.

After coating, herringbone or spiral grooves are cut into the coated metal body using laser ablation. Thus, the process of providing the grooves also removes the corresponding part of the coating. This method of manufacture allows the ridges of the grooved surface to remain coated. Therefore, they are protected against wear. The grooves are not coated, but this is less critical, because the inner surface of the grooves 8 will not be exposed to the mechanical wear.

Advantageously, sufficient pumping action for the bearing to function may be generated whilst also protecting the upper edges of the grooved structure.

According to an embodiment of the invention, a hydrodynamic bearing 1 is provided wherein the first 18 and/or second 24 bearing coatings comprise molybdenum disulphide. Molybdenum disulphide's performance as a solid lubricant is effective in vacuum and up to temperatures of 400° C. Molybdenum disulphide may be deposited by magnetron radiofrequency sputtering to the required thickness. However, other manufacturing techniques can be contemplated.

According to an embodiment of the invention, a hydrodynamic bearing 1 may be provided, wherein the first bearing coating 18 and the second bearing coating 24 comprise at least one material selected from the list of molybdenum disulphide, amorphous carbon, tetrahedrally coordinated amorphous carbon, ultra nano crystalline diamond film, nano- and ultra-nano-crystalline vapour-deposited diamond, polycrystalline diamond, and tungsten disulphide.

The process for producing amorphous carbon is firstly to place in a vacuum vessel for plasma-assisted chemical vapor deposition a gas mixture comprising a gaseous silicon compound, and a gaseous carbon compound as the major components. By discharging this prepared gas atmosphere for film deposition, a hard and lubricant thin film of amorphous carbon is obtained.

According to an alternative embodiment, ultra- and nano-crystalline diamond film can be used on the surface of the bearing. Ultra- and nano-crystalline diamond films have low friction coefficients and high wear resistance.

According to an aspect of the invention, ultra-nano-crystalline diamond may be used in the first, second, or both coatings. Ultra-nano-crystalline diamond is one of the smoothest diamond films available, with a surface having a root mean square roughness of less than 12 nm.

According to an embodiment of the invention, a hydrodynamic bearing 1 is provided wherein the first and/or second bearing coatings comprise a plurality of layers of materials, wherein at least two adjoined layers comprise different materials.

Figure 8A:
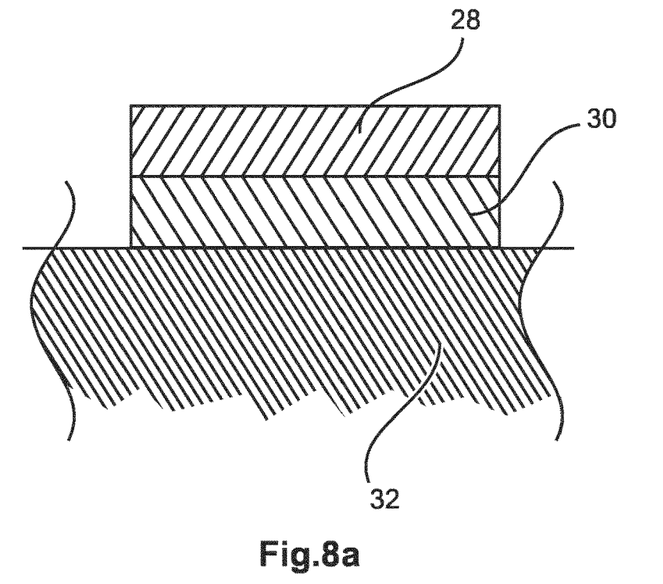
FIGS. 8A and 8B show an X-ray tube show bearing coatings according to an embodiment of the invention.

FIG. 8A illustrates the embodiment previously described. The basis material, such as molybdenum, is shown at feature 32. This may be a portion of the surface of the supporting bushing, or the rotatable shaft. Deposited on top of the basis material 32 is a first material 30. Deposited on top of the first material is a second material 28. The material 30 and the material 28 are different, as shown by the opposed cross-hatching of these layers. According to an embodiment of the invention, a hydrodynamic bearing is provided, wherein the first adjoined layer comprises tetrahedrally-coordinated amorphous carbon, and a second adjoined layer comprises molybdenum disulphide.

Figure 8B:
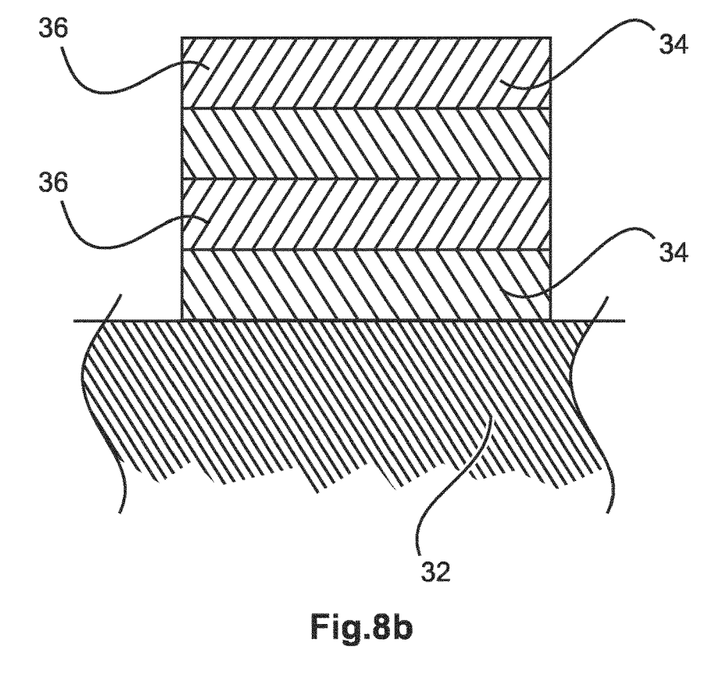

According to an embodiment of the invention, stacks of materials with greater than two layers may be provided. For example, FIG. 8B illustrates a four layer stack of materials. The basis material of molybdenum 32 is coated with a first material 34 and a second material 36, a configuration which is then repeated a second time.

According to an exemplary embodiment of the invention, the layers in the stack of layered coatings used in either the first bearing coating or the second bearing coating may comprise any material, at least from the group of: at least one material selected from the list of molybdenum disulphide, amorphous carbon, tetrahedrally coordinated amorphous carbon, ultra nano crystalline diamond film, nano- and ultra-nano-crystalline vapour-deposited diamond, polycrystalline diamond, and tungsten disulphide. Any combination of the materials in the preceding materials list may be used first bearing coating or second bearing coating.

The stack may comprise several of these materials, in any order. The stack may be ordered in any way. An individual stack may have at least two, three, four, five, six, seven, eight, nine, or ten layers. Any combination of the materials in the preceding materials list may be used in the stack of layers.

According to an embodiment of the invention, the first bearing coating and the second bearing coating may be composed from different stack recipes.

According to an embodiment of the invention, a hydrodynamic bearing is provided, wherein the first bearing coating is substantially resistant to a temperature in the range of 150° C. to 400° C.

According to an embodiment of the invention, a hydrodynamic bearing is provided, wherein the first bearing coating is substantially resistant to a temperature in the range of 150° C. to 500° C.

According to an embodiment of the invention, a hydrodynamic bearing is provided, wherein the first bearing coating is substantially resistant to a temperature in the range of 150° C. to 600° C.

Therefore, advantageously, the first bearing coating will not degrade when exposed to temperatures in these ranges. Other low friction coatings, such as lead, has a comparatively low melting point of 327.5 degrees Celsius.

According to an embodiment of the invention, a hydrodynamic bearing 1 is provided wherein the lubrication material 10 is a gallium-indium-tin alloy. This alloy is a eutectic compound. A eutectic compound is a mixture of chemical compounds that have a single chemical composition that solidifies at a lower temperature than any other composition made up of the same ingredients. This alloy is kept in the bearing gap of the hydrodynamic bearing between the fixed and rotatable bearing parts by the pumping action of the grooves 8.

Figure 9:
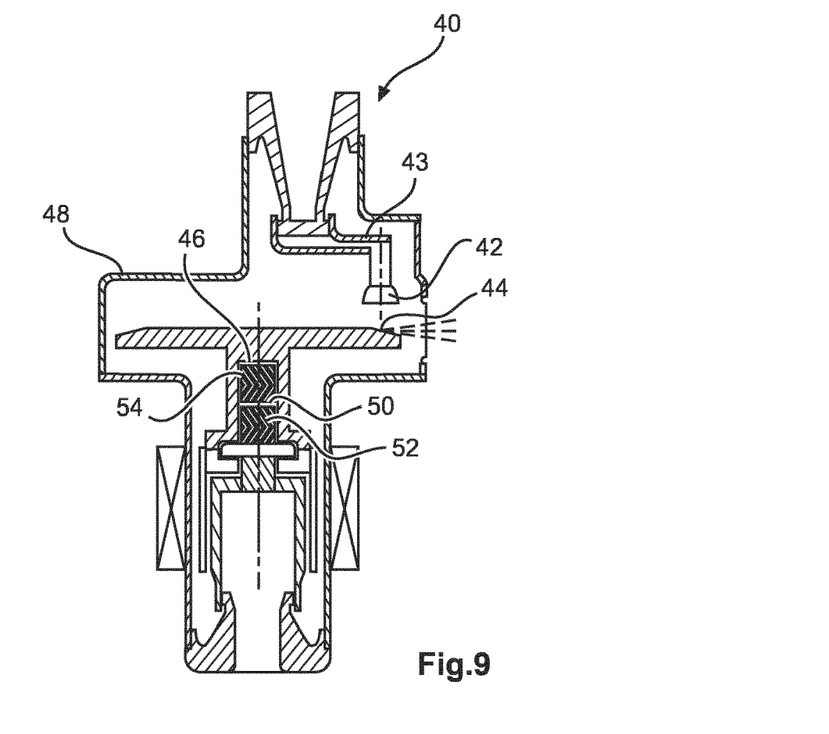
FIG. 9 shows an X-ray tube according to the invention.

According to the invention, an X-ray tube 40 is provided. The X-ray tube comprises a hydrodynamic bearing as previously described, and a cathode 42. The cathode is connected to an anode disc 44. The cathode is configured to emit electrons towards the anode disc, and the anode disc provides a rotatable surface which is configured to generate X-rays as a result of electrons, emitted by the cathode, impinging on the rotatable disc.

FIG. 9 shows an X-ray tube 40 according to the invention. The X-ray tube 40 comprises a metal frame 48 to which the cathode 42 is connected via the cathode isolator 43. The anode comprises an anode disc 44, and is designed as a rotatable-anode. The anode is connected to the metal frame 46 via an anode isolator. The cathode 42 is adapted for emitting electrons towards the anode disc 44, while the anode disc 44 provides a rotatable surface which generates X-rays as a result of electrons emitted by the cathode 42 impinging on the anode disc. The X-rays may leave the metal frame 48 through an X-ray window, for example, made of beryllium. The rotatable anode disc is supported by the hydrodynamic bearing 1, 46, and is connected to the anode isolator. The bearing shaft is connected to a support and is concentrically enclosed by the bearing bushing. Furthermore, the bearing bushing is connected to a rotor, such that the anode disc rotates when power is provided to the X-ray tube 40. The bearing shaft comprises a bore, parallel to the longitudinal axis of the hydrodynamic bearing, in which a cooling fluid may circulate.

Alternatively, the anode disc may be connected to the rotatable shaft, and the bearing may be stationary.

The rotatable shaft 54 is provided with a pattern of grooves 50 and 52. The grooves and the bearing gap between the rotatable shaft and the supporting bushing may be filled with a metal eutectic material acting as a lubrication material. During the rotation of the anode in a prescribed direction of rotation, the groove pattern in the bearing acts as a pump to maintain the eutectic inside the bearing gap. The pressure distribution in the eutectic lubrication material 10 may take up forces acting radially on the hydrodynamic bearing 40.

As previously discussed, first bearing surface portions and second bearing surface portions arranged opposite to each other in the hydrodynamic bearing may, at least in part, be coated with a first bearing coating, having a lower coefficient sliding friction than a higher wear resistance, compared to a basis material of the rotatable shaft and/or a basis material of the supporting bushing.

Therefore, in an X-ray tube comprising a hydrodynamic bearing according to the invention, damage to surfaces of the bearing can be avoided during a starting and a landing phase of the rotatable anode. Such protection afforded to the surfaces inside the bearing lead to the provision of an X-ray tube with a longer operating life and a tolerance for higher bearing rotation velocity.

Figure 10:
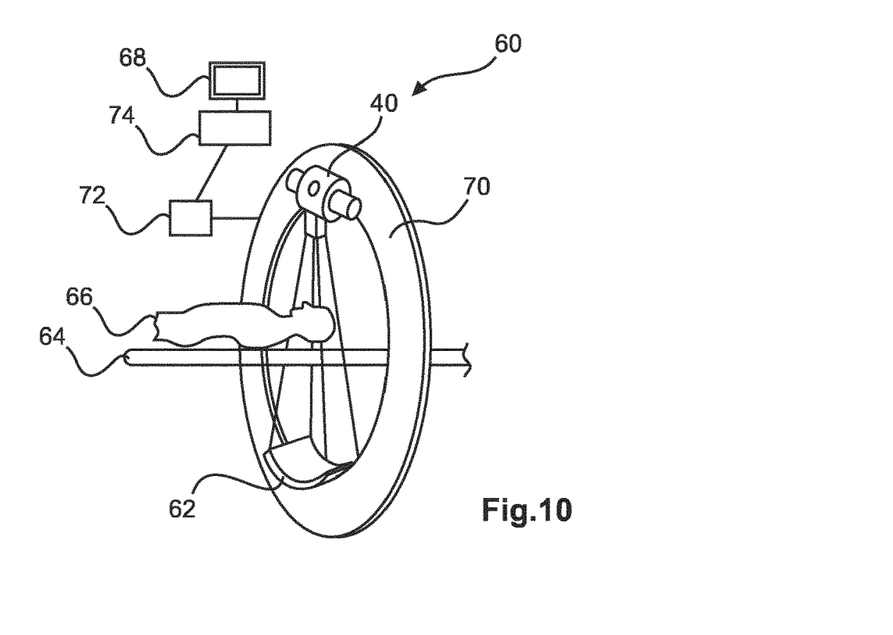
FIG. 10 shows an X-ray system comprising an X-ray tube with a hydrodynamic bearing according to the invention.

According to the invention, an X-ray imaging system 60 according to the invention is provided. The system comprises an X-ray tube 40 comprising a hydrodynamic bearing, as previously described. In addition, the X-ray imaging system 60 comprises an X-ray detector 62, a support 64 for receiving an object 66, and a processing device 68. The X-ray tube 40 is adapted for generating X-ray radiation. Additionally, the X-ray detector is adapted to receive the X-ray radiation after the radiation passes the object on the support.

FIG. 10 illustrates an X-ray imaging system according to the invention. In FIG. 10, the X-ray imaging system 60 is implemented as a CT system. with the CT system comprises an X-ray tube 40 incorporating a hydrodynamic bearing as previously described, and an X-ray detector 62. The X-ray tube 40 and the X-ray detector 62 are arranged on gantry 70. The gantry 70 provides a rotational movement of the tube 40 and the detector 62 with respect to an object 66. The imaging system 60 further comprises a support 64 for receiving the object 66. The object 66 may, for example, be a patient. The X-ray tube 40 is adapted to generate X-ray radiation and the X-ray detector 62 is adapted to receive the X-ray radiation after the radiation passes through the object 66 on the support 70.

The processing device 68 is adapted to control the X-ray radiation by controlling the velocity of the rotor connected to the anode disc, depending on a load acting on the hydrodynamic bearing 1.

Moreover, in an aspect of the invention, the X-ray imaging system may comprise a display 68 and an interface device 72 connected to the processing device 74. The display 68 may serve as a source of information for controlling the X-ray imaging system 60, as well as for showing the image results acquired by the X-ray detector 62.

In a further exemplary embodiment of the invention, the X-ray tube 40 and the X-ray detector 62 may be arranged on opposing ends of a C-arm. A C-arm may enable different trajectories of the X-ray tube 40 and the X-ray detector 62 around the object 66 besides the rotational movement.

Figure 11:
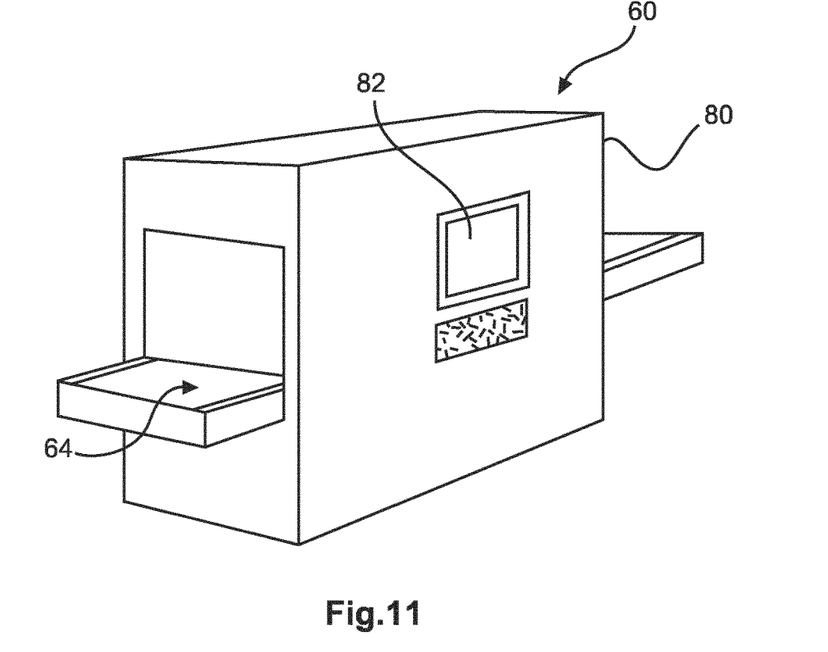
FIG. 11 also shows an X-ray system according to the invention.

FIG. 11 shows the X-ray imaging system 60 according to the invention as a luggage inspection device. The luggage inspection device comprises a housing 80 through which support 64 designed as a conveyer belt passes. Objects 66 such as suitcases may be positioned on the support. Furthermore, a display interface device 82 is arranged at a side of the housing. Inside the housing, an X-ray tube according to the examples described above is provided, as well as an X-ray detector 62. Additionally, a processing device 74 is provided to control the X-ray imaging system.

Figure 12:
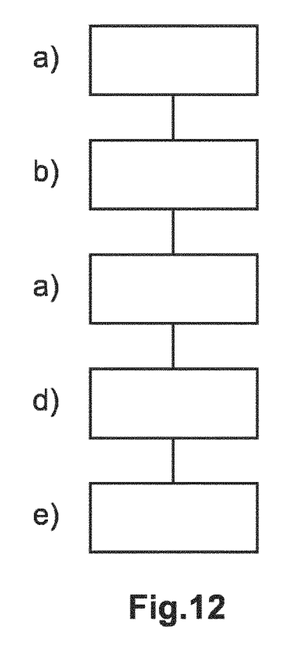
FIG. 12 shows a method of manufacturing a hydrodynamic bearing according to the invention.

In FIG. 12, the steps of a method for manufacturing a hydrodynamic bearing 1 are schematically shown according to an exemplary embodiment of the invention.

In a first step (a), an untreated rotatable bearing shaft and supporting bushing parts are provided.

In a further step (b), a first bearing coating is deposited on at least a part of either the untreated rotatable shaft, the untreated supporting bushing, or both, wherein the first coating has a lower coefficient of sliding friction and a higher wear resistance, compared to a basis material of the rotatable shaft and/or a basis material of the supporting bushing.

In step (c), the rotatable shaft and supporting bushing parts are assembled into a hydrodynamic bearing.

In a further step (d), a lubrication material is added to the hydrodynamic bearing.

Finally, in step (e), the bearing is vacuum sealed.

According to an exemplary embodiment of the invention, a method for manufacturing a hydrodynamic bearing for an X-ray tube is provided wherein, in-between step (b) and (c), there is a further step (b1), of pre-treating either the rotatable bearing shaft, the supporting bushing parts, or both, to improve their compatibility with the lubrication material.

The pre-treatment may be done by heating in the presence of the lubrication material 10, by chemical treatment, by abrasive blasting, as previously discussed, or by other methods known to those skilled in the art.

It should be noted that embodiments of the invention are described with references to different subject-matters. In particular some embodiments are described with reference to method type claims, whereas other embodiments are described with reference to device type claims. However, a person skilled in the art will gather from the above and following description that, unless otherwise notified, in addition to any combination of features belong to one type of the subject-matter, also any combination between features related to different subject-matter is considered to be disclosed with this application. However, all features can be combined providing synergetic effects that are more than a simply summation of the features.

While the invention has been illustrated and described in detail in the drawings and foregoing description, such illustration and description are to be considered illustrative or exemplary, and not restrictive. The invention is not limited to the disclosed embodiments. Other variations to the disclosed embodiments can be understood and effected by

The invention claimed is:

1. A hydrodynamic bearing for an X-ray tube with a rotatable anode, comprising:
   a rotatable shaft for supporting the rotatable anode;
   a supporting bushing arranged to seal a length of the shaft; and
   a bearing arrangement provided between the shaft and the supporting bushing, comprising a primary bearing mechanism and a secondary bearing mechanism;
   wherein the shaft is rotatably supported by the bearing arrangement in relation to the bushing;
   wherein the primary bearing mechanism comprises a plurality of grooves in a surface of the supporting bushing and/or the shaft, and a lubrication material contained within a sealed space between the rotatable shaft and the supporting bushing; wherein the grooves are operable to interact with the lubrication material; and wherein the primary bearing mechanism supports the rotatable shaft during a steady operating phase of the rotatable anode;
   wherein the secondary bearing mechanism comprises first bearing surface portions on the surface of the supporting bushing and second bearing surface portions on the rotatable shaft; wherein the first and second bearing surface portions are arranged opposite to each other; wherein the first and second bearing surface portions are provided as mutual contact surface portions; wherein the secondary bearing mechanism supports the rotatable shaft during a starting and a landing phase of the rotatable anode; and wherein the first and second bearing surface portions of the secondary bearing mechanism do not contact each other during the steady operating phase;
   wherein at least a part of the first and/or second bearing surface portions comprises a first and/or second bearing coating having a lower coefficient of sliding friction and a higher wear resistance, compared to a basis material of the rotatable shaft and/or a basis material of the supporting bushing; and
   wherein the first and/or second bearing coatings compromise a plurality of layers of materials, wherein at least two adjoined layers comprise different materials, wherein a first adjoined layer comprises tetrahedral coordinated amorphous carbon (t-aC) and a second adjoined layer comprises molybdenum disulphide ($MoS_2$).

2. Hydrodynamic bearing of claim 1, wherein the first bearing surface portion and the second bearing surface portion are coated with the first bearing coating, and the coated portions are arranged opposite to each other.

3. Hydrodynamic bearing according to claim 1, wherein the second bearing surface portion comprises a second bearing coating different in composition to the first bearing coating.

4. Hydrodynamic bearing according to claim 1, wherein at least one bearing coating is treated for compatibility with the lubrication material.

5. Hydrodynamic bearing according to claim 1, wherein the grooves comprise upper ridges, and the upper ridges are treated with the first bearing coating.

6. Hydrodynamic bearing according to claim 5, wherein the first and/or second bearing coatings comprise molybdenum disulphide.

7. Hydrodynamic bearing according claim 6, wherein the first and second bearing coatings comprise at least one material selected from the list of molybdenum disulphide, amorphous carbon, tetrahedrally coordinated amorphous carbon, ultra nano crystalline diamond film, nano- and ultra-nano-crystalline vapour-deposited diamond, polycrystalline diamond, and tungsten disulphide.

8. Hydrodynamic bearing of claim 1, wherein the first bearing coating is substantially resistant to a temperature in the range 150° C. to 400° C.

9. Hydrodynamic bearing of claim 8, wherein the lubrication material is a Ga—In—Sn alloy.

10. An X-ray tube, comprising:
    a hydrodynamic bearing according to claim 9; and
    a cathode;
    wherein the cathode is configured to emit electrons towards an anode disc;
    wherein the anode disc provides a rotatable surface which is configured to generate X-rays as a result of electrons, emitted by the cathode, impinging on the rotatable disc.

11. An X-ray imaging system, comprising:
    an X-ray tube according to claim 10;
    an X-ray detector;
    a support for receiving an object; and
    a processing device;
    wherein the X-ray tube is adapted for generating X-ray radiation;
    wherein the X-ray detector is adapted to receive the X-radiation after the radiation passes the object on the support.

12. A method for manufacturing a hydrodynamic bearing for an X-ray tube, comprising the steps of:
    (a) providing untreated rotatable shaft and supporting bushing parts;
    (b) depositing a first and/or second bearing coating on at least a part of either the untreated rotatable shaft, the untreated supporting bushing, or both, wherein the first coating has a lower coefficient of sliding friction and a higher wear resistance, compared to a basis material of the rotatable shaft and/or a basis material of the supporting bushing, wherein the first and/or second bearing coatings comprise a plurality of layers of materials, wherein at least two adjoined layers comprise different materials, wherein a first adjoined layers comprise tetrahedral coordinated amorphous carbon (t-aC) and a second adjoined layer comprises molybdenum disulphide ($MoS_2$);
    (c) assembling the rotatable shaft and supporting bushing parts into a hydrodynamic bearing;
    (d) adding a lubrication material;
    (e) vacuum sealing the bearing.

13. Method according to claim 12, wherein in-between step b) and step c), there is the further step of:
    (b1) pre-treating either the bearing shaft, the bearing bushing parts, or both, to improve their compatibility with the lubrication material.

* * * * *